(12) United States Patent
Liu et al.

(10) Patent No.: US 10,337,018 B1
(45) Date of Patent: Jul. 2, 2019

(54) ASPARAGINASE MUTANT WITH EFFICIENT EXPRESSION, ACTIVITY AND STABILITY

(71) Applicant: Jiangnan University, Wuxi (CN)

(72) Inventors: Song Liu, Wuxi (CN); Jian Chen, Wuxi (CN); Guocheng Du, Wuxi (CN); Weixin Zhao, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/177,480

(22) Filed: Nov. 1, 2018

(51) Int. Cl.
  *C12N 9/82* (2006.01)
  *C12N 15/52* (2006.01)
  *C12N 1/14* (2006.01)
  *C12N 1/20* (2006.01)

(52) U.S. Cl.
  CPC ............... *C12N 15/52* (2013.01); *C12N 1/14* (2013.01); *C12N 1/20* (2013.01); *C12N 9/82* (2013.01); *C12Y 305/01001* (2013.01)

(58) Field of Classification Search
  None
  See application file for complete search history.

(56) References Cited

U.S. PATENT DOCUMENTS

2017/0145401 A1* 5/2017 Liu .................. C12N 9/82

OTHER PUBLICATIONS

GenBank Accession No. WP_052897644.1, published Aug. 16, 2017 (Year: 2017).*

* cited by examiner

*Primary Examiner* — Richard C Ekstrom
(74) *Attorney, Agent, or Firm* — Na Xu; IPro, PLLC

(57) ABSTRACT

The present disclosure discloses an asparaginase mutant with efficient expression, activity and stability, belonging to the technical fields of gene engineering and enzyme engineering. The amino acid sequence of the asparaginase mutant is set forth in SEQ ID NO: 99, SEQ ID NO: 100 or SEQ ID NO: 101; meanwhile, compared with the wild type asparaginase mutant, the extracellular enzyme activity of the asparaginase fusion enzyme mutant is increased by up to 2.25 times, the stability is increased by up to 3.56 times, and the specific enzyme activity is increased by up to 1.34 times.

8 Claims, 4 Drawing Sheets

Specification includes a Sequence Listing.

ASPARAGINASE MUTANT WITH EFFICIENT EXPRESSION, ACTIVITY AND STABILITY

TECHNICAL FIELD

The present disclosure relates to an asparaginase mutant with efficient expression, activity and stability, belonging to the technical fields of gene engineering and enzyme engineering.

BACKGROUND

Obtaining high-expression high-heat-stability enzymes based on the important influence of expression amount and heat stability on the application performance of enzymes has been the research hotspot in the field of enzyme engineering.

There is a certain mutual promotion relationship among expression level, heat stability and enzyme catalytic activity. In terms of expression level, the prior art generally increases the expression level of protease by the optimization of the expression element or the fusion of expression tags at the terminal, but the optimization of the expression element has certain uncertainty, and the most commonly used expression tags, such as MBP, GST and other macromolecules, all have certain effects on the late application of the enzyme, and often require complex procedures to be removed. In terms of stability, with the development of structural biology and bioinformatics, researchers can accurately locate the amino acid residues or peptides that affect the heat stability of the enzyme molecules by analysis of some structural parameters (such as B-factor, RMSF value, etc.) or comparison of homologous sequences, so that site-directed mutagenesis is carried out to enhance the heat stability of enzymes. Although it has become a conventional strategy for the heat stability modification of enzymes, the above molecular modification technology still has inherent technical defects. The premise of site-directed mutagenesis is to obtain accurate information on the molecular structure of the enzyme, so in vitro directed evolution is faced with a large number of mutant screenings, resulting in the difficulty in obtaining mutants with significantly improved heat stability in a short period of time.

Therefore, the establishment of an efficient and convenient enzyme stabilization strategy has become the focus of researchers at home and abroad.

It is worth noting that the increase in the expression level and heat stability of the enzyme by the fusion short peptide is accomplished under the conditions of no enzyme structure information and a large number of mutant screenings, and the efficiency is significantly improved as compared with the traditional molecular modification technology. It was first discovered by the Urabe team at Osaka University in Japan when studying the heat stability of Bacillus stearothermophilus catalase (Nat Biotechnol, 1999, 17(1): 58-61); the researchers randomly fused short peptides of different lengths and amino acid sequences at the C-terminal of catalase to obtain a series of high-heat-stability mutants; and then, the Kanaya team at Osaka University discovered that the fusion of the Pyrococcus horikoshii ribonuclease C-terminal heptapeptide (IGCIILT) at the C-terminal can improve the heat stability of ribonuclease from different sources to different degrees (PLoS ONE, 2011, 6(1): e16226).

SAPs are a category of short peptides with alternately distributed hydrophilic and hydrophobic amino acids that can be spontaneously assembled into nanostructures. Due to unique amphipathic properties, the short peptides can form hydrogels in water, thereby immobilizing the target proteins or other small molecules. Based on this, in the preliminary study of this laboratory (Appl Microbiol Biot, 2013, 97(21): 9419-9427), a category of SAPs were fused to the N-terminal of the enzyme for heterologous expression of the fusion enzyme, and it was found that SAPs have the function of increasing the expression level and stability of enzymes, and S1 (AEAEAKAKAEAEAKAK) with special charge distribution has certain universal effects; Lin et al. (Faraday Discuss, 2013,166:233) of Tsinghua University used SAP (LELELKLKLELELKLK), which is similar to the amino acid composition of S1, to fuse at the end of the enzyme, which can promote the formation of active inclusion bodies, indicating that the amino acid composition has an important influence on the secretion expression and stability of SAPs fusion protein. On the other hand, the composition of the linker between SAPs and the enzyme also plays an important role in the expression and stability of the fusion enzyme (Enzyme Microb Tech, 2016,82:105-109).

The present disclosure attempts to construct a polypeptide library based on SAPs to quickly, efficiently and conveniently obtain an enzyme mutant having high expression, high activity and high stability.

SUMMARY

The object of the present disclosure is to provide an asparaginase mutant with efficient expression, activity and stability. The mutant is based on a functional polypeptide library constructed on the basis of SAPs, and the whole process of obtaining the enzyme mutant is fast, efficient and convenient; meanwhile, compared with the wild type alkaline pectinase, the extracellular enzyme activity of the alkaline pectinase mutant obtained by using this functional polypeptide library is increased by up to 15.32 times, the stability is increased by up to 3.86 times, and the specific enzyme activity is increased by up to 2.55 times; the intracellular enzyme activity of the lipoxygenase fusion enzyme mutant is increased by up to 2.49 times, the stability is increased by up to 3.82 times, and the specific enzyme activity is increased by up to 0.49 time; and the extracellular enzyme activity of the asparaginase fusion enzyme mutant is increased by up to 2.33 times, the stability is increased by up to 1 time, and the specific enzyme activity is increased by up to 1.17 times.

The present disclosure provides an enzyme mutant, the parent amino acid sequence of the wild-type asparaginase is set forth in SEQ ID NO. 6.

The present disclosure provides an enzyme mutant, the parent amino acid sequence of the wild-type asparaginase is set forth in SEQ ID NO. 7.

The present disclosure provides an enzyme mutant, the parent amino acid sequence of the wild-type asparaginase is set forth in SEQ ID NO: 8.

In one embodiment of the present disclosure, wherein said the amino acid sequence of the asparaginase mutant is set forth in SEQ ID NO: 99.

In one embodiment of the present disclosure, wherein said the amino acid sequence of the asparaginase mutant is set forth in SEQ ID NO: 100.

In one embodiment of the present disclosure, wherein said the amino acid sequence of the asparaginase mutant is set forth in SEQ ID NO: 101.

The present disclosure provides the gene encoding the above asparaginase mutant with efficient expression, activity and stability.

The present disclosure provides the recombinant plasmid carrying the above gene.

In one embodiment of the present disclosure, wherein said the expression plasmid vector of the recombinant plasmid is pUC, pET or pGEX.

In one embodiment of the present disclosure, wherein said the expression plasmid vector of the recombinant plasmid is pET.

The present disclosure provides the host cell carrying the above gene, or the above recombinant plasmid.

The present disclosure provides application of the above asparaginase mutant with efficient expression, activity and stability, or the above gene, or the above recombinant plasmid in the preparation of drugs.

The present disclosure provides a method for obtaining an enzyme mutant having high expression, high activity and high stability, characterized by comprising the following steps:

step 1: constructing a functional polypeptide library;

step 2: performing preliminary screening on expression host cells obtained from the functional polypeptide library in step 1 by using the fluorescence intensity as screening criteria to obtain host cells with high fluorescence intensity;

step 3: culturing the host cells with high fluorescence intensity obtained after the preliminary screening in step 2, and performing re-screening and identification by using the fluorescence intensity as screening criteria to obtain host cells with high fluorescence intensity;

step 4: performing fluorescent protein expression gene deletion on an expression vector in the host cells with high fluorescence intensity obtained by re-screening in step 3, and performing heterologous expression on the deleted expression vector to obtain enzyme mutants; and step 5: performing heat treatment and stability determination on the obtained enzyme mutants to screen out an enzyme mutant having high stability;

the functional polypeptide library in step 1 is obtained by expression of host cells containing the functional expression vector; and the functional expression vector comprises a self-assembling amphipathic peptides (SAPs) of different lengths and amino acid compositions, linkers of different lengths and different rigidities and flexibilities, a fluorescent protein expression gene and a to-be-screened enzyme expression gene.

In one embodiment of the present disclosure, the preliminary screening in step 2 is performed by using a flow cytometer.

The present disclosure provides a functional polypeptide library for obtaining an enzyme mutant having high expression, high activity and high stability, and the functional polypeptide library is obtained by expression of host cells containing the functional expression vector; and the functional expression vector comprises a self-assembling amphipathic peptides (SAPs) of different lengths and amino acid compositions, linkers of different lengths and different rigidities and flexibilities, a fluorescent protein expression gene and a to-be-screened enzyme expression gene.

In one embodiment of the present disclosure, the SAP is linked to the 5' end of the to-be-screened enzyme expression gene by a linker.

In one embodiment of the present disclosure, the fluorescent protein expression gene is fused at the 3' end of the to-be-screened enzyme expression gene.

In one embodiment of the present disclosure, the SAP is SAP obtained by coding the gene with the sequence of SEQ ID NO. 1 and/or SAPs obtained by performing further random mutation of length and amino acid by using the SAP obtained by coding the gene with the sequence of SEQ ID NO. 1 as a template.

In one embodiment of the present disclosure, the linker comprises different rigid peptide and flexible peptide combination units.

In one embodiment of the present disclosure, the amino acid sequences of the rigid peptide and flexible peptide combination units are respectively SEQ ID NO. 2 and SEQ ID NO. 3.

In one embodiment of the present disclosure, the rigid peptide and flexible peptide combination units are respectively obtained by coding genes with sequences of SEQ ID NO. 4 and SEQ ID NO. 5.

In one embodiment of the present disclosure, the length of the rigid peptide and flexible peptide combinations in the linker is 1 to 5 units.

In one embodiment of the present disclosure, the combinations of the rigid peptide and flexible peptide in the linker comprise the contents shown in Table 1.

TABLE 1

Table of linker sequences

| No. | Linker sequences | No. | Linker sequences |
|---|---|---|---|
| 1 | SEQ ID NO.9 | 2 | SEQ ID NO.10 |
| 3 | SEQ ID NO.11 | 4 | SEQ ID NO.12 |
| 5 | SEQ ID NO.13 | 6 | SEQ ID NO.14 |
| 7 | SEQ ID NO.15 | 8 | SEQ ID NO.16 |
| 9 | SEQ ID NO.17 | 10 | SEQ ID NO.18 |
| 11 | SEQ ID NO.19 | 12 | SEQ ID NO.20 |
| 13 | SEQ ID NO.21 | 14 | SEQ ID NO.22 |
| 15 | SEQ ID NO.23 | 16 | SEQ ID NO.24 |
| 17 | SEQ ID NO.25 | 18 | SEQ ID NO.26 |
| 19 | SEQ ID NO.27 | 20 | SEQ ID NO.28 |
| 21 | SEQ ID NO.29 | 22 | SEQ ID NO.30 |
| 23 | SEQ ID NO.31 | 24 | SEQ ID NO.32 |
| 25 | SEQ ID NO.33 | 26 | SEQ ID NO.34 |
| 27 | SEQ ID NO.35 | 28 | SEQ ID NO.36 |
| 29 | SEQ ID NO.37 | 30 | SEQ ID NO.38 |
| 31 | SEQ ID NO.39 | 32 | SEQ ID NO.40 |
| 33 | SEQ ID NO.41 | 34 | SEQ ID NO.42 |
| 35 | SEQ ID NO.43 | 36 | SEQ ID NO.44 |
| 37 | SEQ ID NO.45 | 38 | SEQ ID NO.46 |
| 39 | SEQ ID NO.47 | 40 | SEQ ID NO.48 |
| 41 | SEQ ID NO.49 | 42 | SEQ ID NO.50 |
| 43 | SEQ ID NO.51 | 44 | SEQ ID NO.52 |
| 45 | SEQ ID NO.53 | 46 | SEQ ID NO.54 |
| 47 | SEQ ID NO.55 | 48 | SEQ ID NO.56 |
| 49 | SEQ ID NO.57 | 50 | SEQ ID NO.58 |
| 51 | SEQ ID NO.59 | 52 | SEQ ID NO.60 |
| 53 | SEQ ID NO.61 | 54 | SEQ ID NO.62 |
| 55 | SEQ ID NO.63 | 56 | SEQ ID NO.64 |
| 57 | SEQ ID NO.65 | 58 | SEQ ID NO.66 |
| 59 | SEQ ID NO.67 | 60 | SEQ ID NO.68 |
| 61 | SEQ ID NO.69 | 62 | SEQ ID NO.70 |

The present disclosure provides a method for constructing the functional polypeptide library for obtaining an enzyme mutant having high expression, high activity and high stability, characterized by comprising the following steps:

step 1: introducing a plurality of multiple cloning sites to multiple cloning sites of the expression vector to modify the expression vector;

step 2: sequentially introducing the to-be-screened enzyme expression gene, SAP and fluorescent protein expression gene into the multiple cloning sites of the modified expression vector obtained in step 1;

step 3: introducing a linker gene upstream of the to-be-screened enzyme expression gene introduced in step 2 such that the SAP is linked to the to-be-screened enzyme expression gene by the linker to obtain a functional expression vector; and step 4: transforming the functional expression vector obtained in step 3 into an expression host cell for heterologous expression to obtain the functional polypeptide library.

In one embodiment of the present disclosure, a backbone of the expression vector is pET-22b(+).

In one embodiment of the present disclosure, the number of the multiple cloning sites introduced in step 1 is four.

In one embodiment of the present disclosure, step 2 is to link the SAP to the 5' end of the to-be-screened enzyme gene by the linker and fuse the fluorescent protein expression gene to the 3' end of the to-be-screened enzyme expression gene.

In one embodiment of the present disclosure, step 2 is to linearize the expression vector by PCR and introduce SAP mutation to the upstream region of the to-be-screened enzyme expression gene by using degenerate primers.

In one embodiment of the present disclosure, step 3 is to perform PCR on the linker gene by using the primer containing the homologous arm of step 2, amplify the linker by using a recombinant plasmid linked with different linkers as a template and finally fuse the linker between the SAP and the to-be-screened enzyme expression gene such that the SAP is linked to the to-be-screened enzyme expression gene by the linker, thereby obtaining the functional expression vector.

In one embodiment of the present disclosure, the recombinant plasmid is pMD-18T.

Beneficial Effects (1) According to the enzyme mutant obtained by the present disclosure, compared with the wild type alkaline pectinase, the extracellular enzyme activity of the fused enzyme mutant of the alkaline pectinase mutant is increased by up to 15.32 times, the stability is increased by up to 3.86 times, and the specific enzyme activity is increased by up to 2.55 times; the intracellular enzyme activity of the lipoxygenase fusion enzyme mutant is increased by up to 2.49 times, the stability is increased by up to 3.13 times, and the specific enzyme activity is increased by up to 0.9 time; and the extracellular enzyme activity of the asparaginase fusion enzyme mutant is increased by up to 2.25 times, the stability is increased by up to 3.56 times, and the specific enzyme activity is increased by up to 1.34 times.

(2) By combining the composition characteristics of the SAPs and the composition characteristics of the linkers, the present disclosure is applied to screening of the expression level and stability of enzymes and screening of catalytic activity, substrate affinity or comprehensive results.

(3) The capacity of the functional polypeptide library constructed by the present disclosure can reach 106 or more, the positive mutation rate can reach 86%, and the mutation types are balanced (as shown in FIG. 2).

(4) By using GFP as the expression level screening tag, the screening method is simple, can perform high-throughput screening, and has wide application in the aspect of modification of expression level and stability of enzymes.

(5) The present disclosure uses a flow cytometer to perform high-throughput screening of fluorescent cells. The flow cytometer screening technique has the advantages of high speed, high precision and high accuracy, and is one of the most advanced cell quantitative analysis techniques in the modern era.

DETAILED DESCRIPTION

Figure 1:
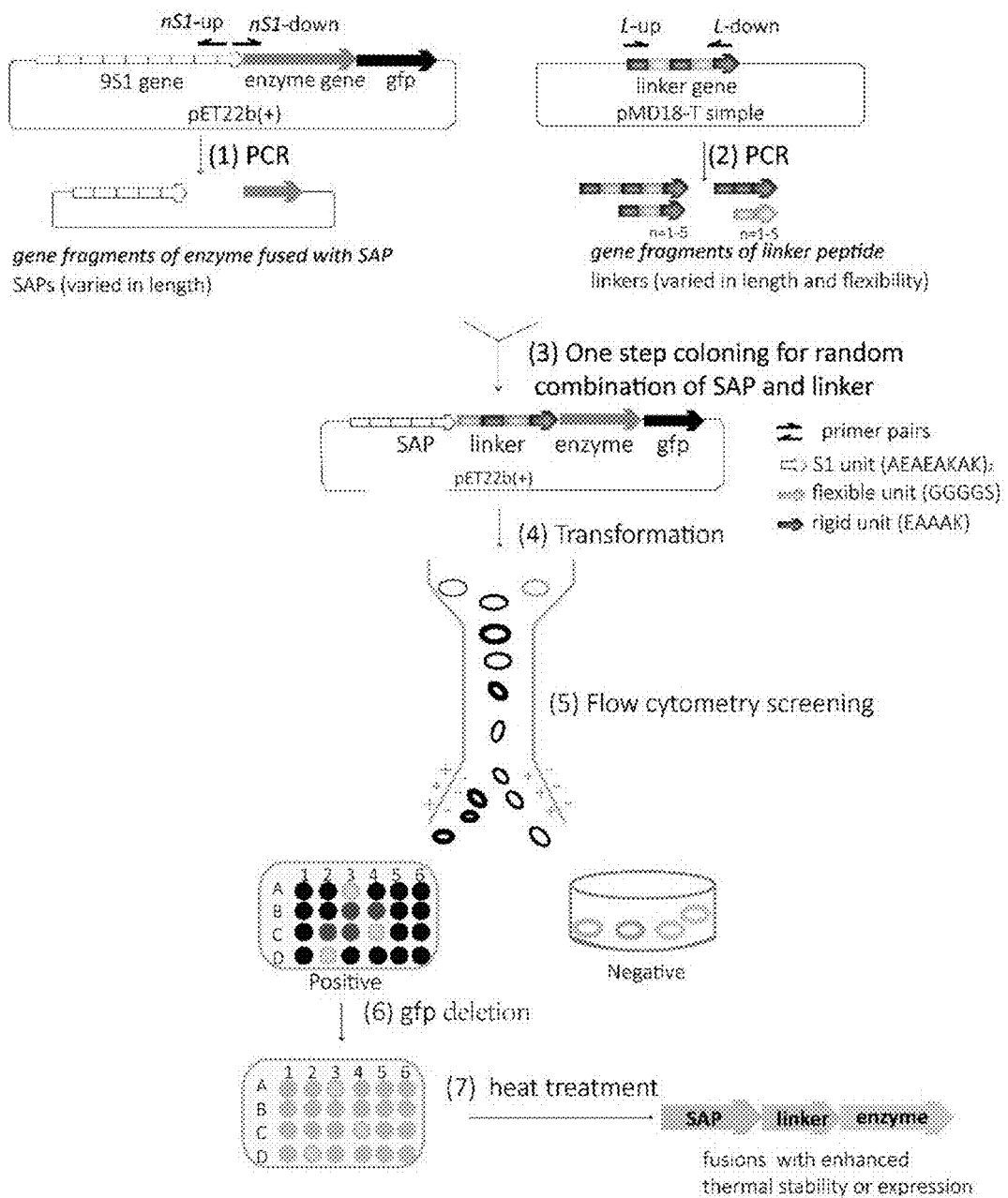
FIG. 1 is a schematic diagram showing the construction of a functional polypeptide library of the present disclosure.
Figure 2:
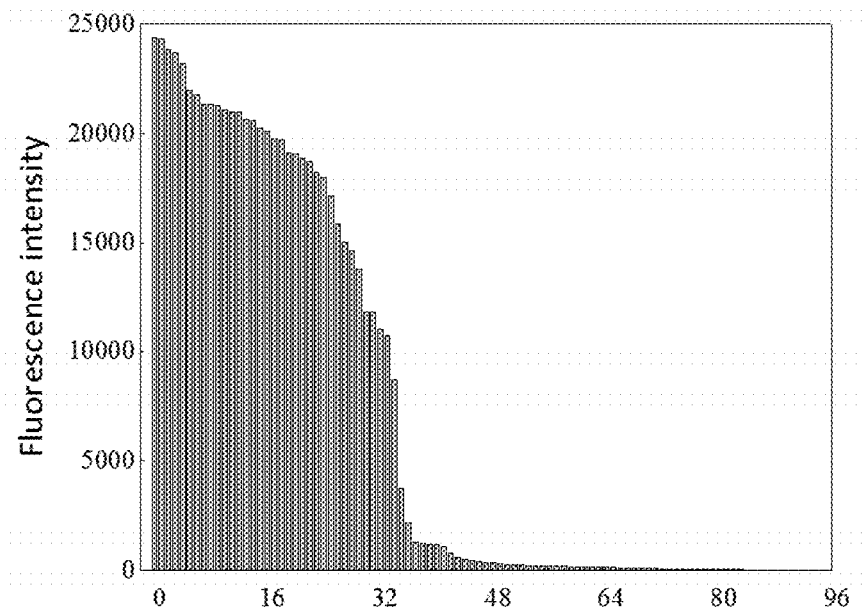
FIG. 2. Expression level in one 96-deep well plate measured by fluorescence intensity.
Figure 3:
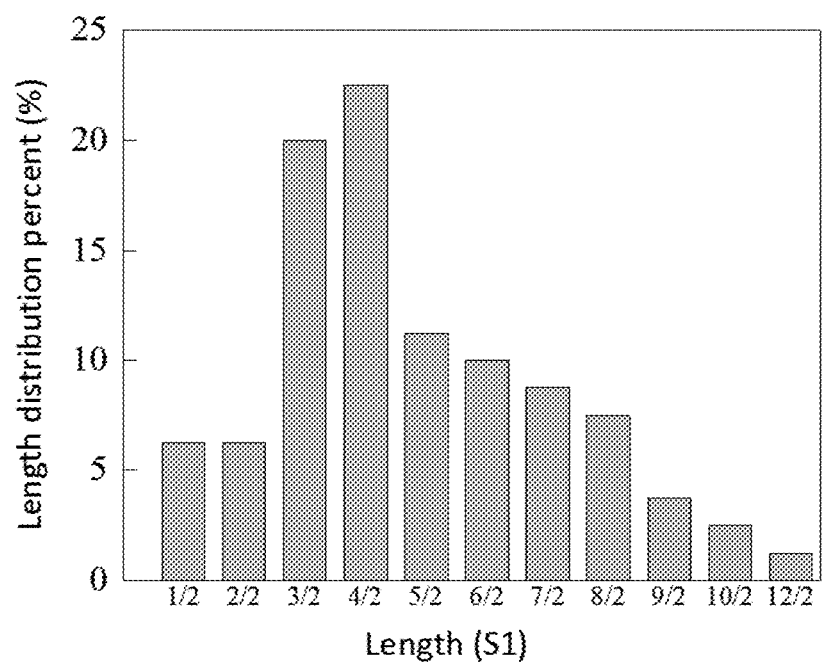
FIG. 3. SAP length distribution.
Figure 4:
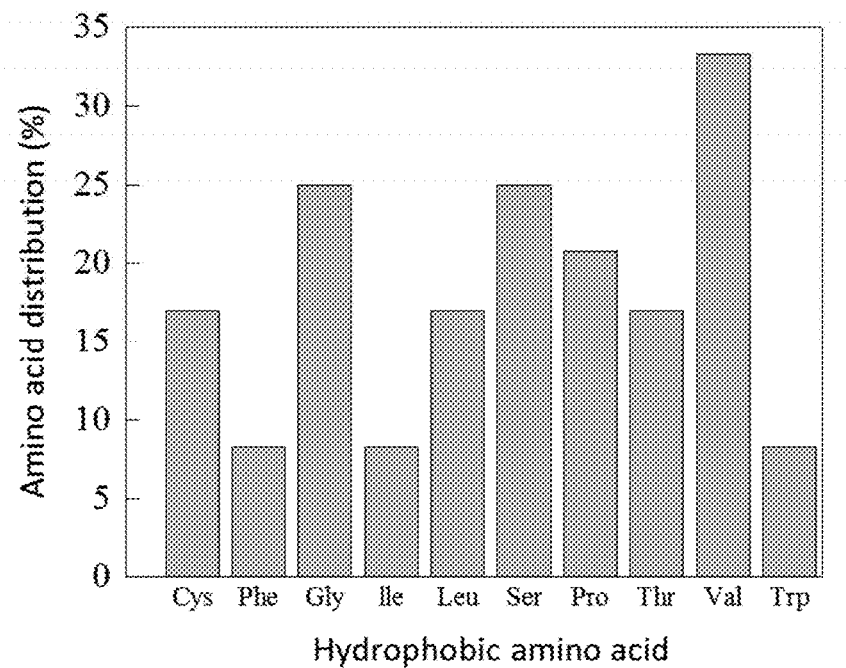
FIG. 4. Hydrophobic amino acid distribution.
Figure 5:
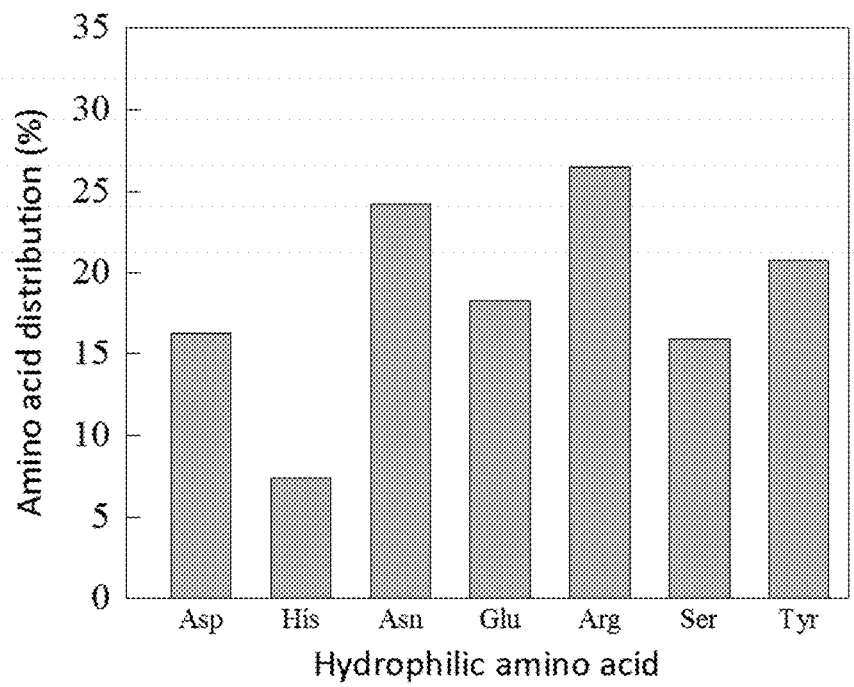
FIG. 5. Hydrophilic amino acid distribution.
Figure 6:
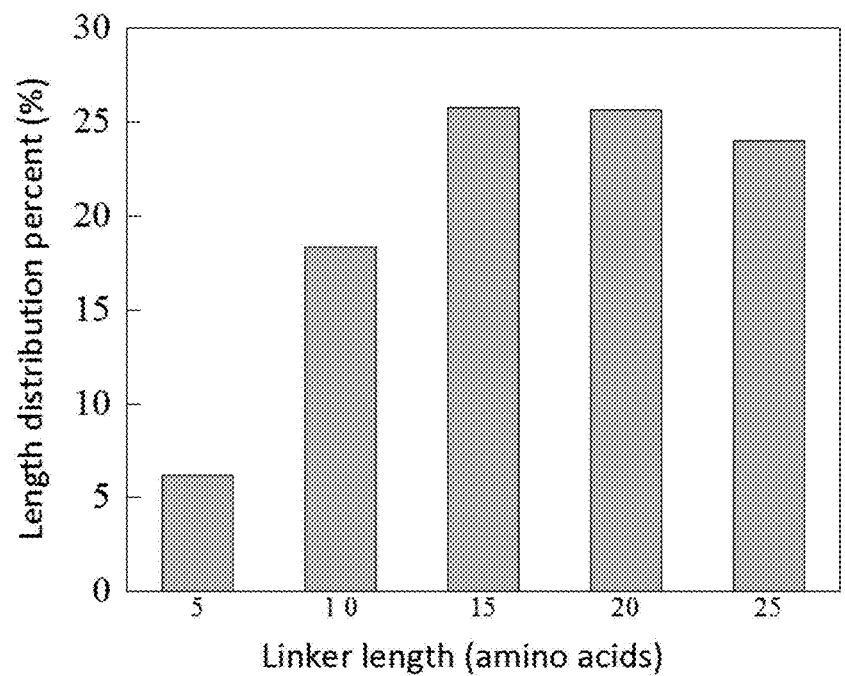
FIG. 6. Linker length distribution.
Figure 7:
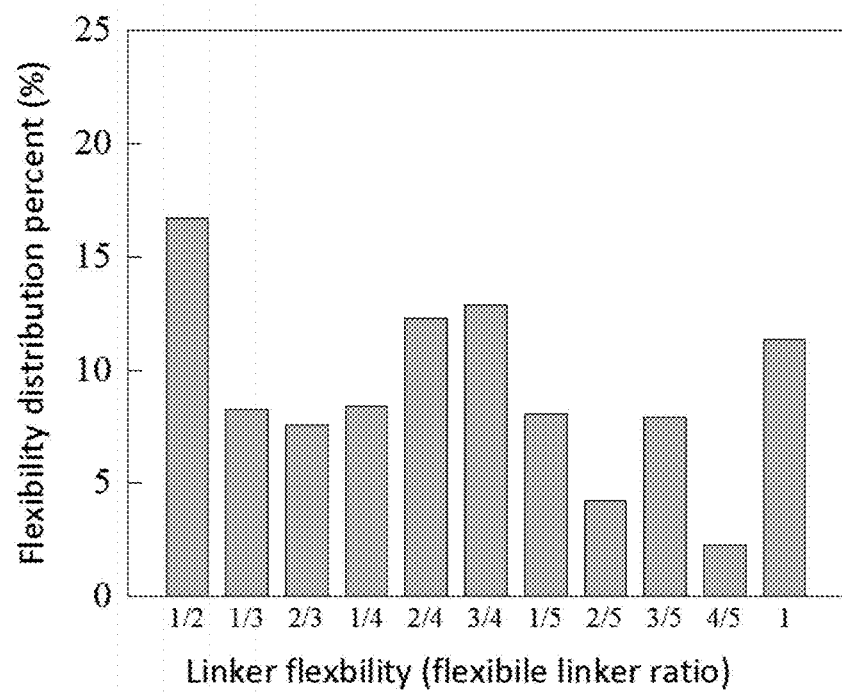
FIG. 7. Linker flexibility distribution.

The following are embodiments of the present disclosure, but are not intended to limit the present disclosure in any way.

The culture method, purification method and enzymatic properties of the relevant fusion enzyme expression strains in the present disclosure are shown below.

Culture Medium Composition (g/L):

Seed medium: peptone 10, yeast extract 5 and sodium chloride 5;

Fermentation medium: the following components were dissolved in 0.9 L of water: peptone 12 g, yeast extract 24 g and glycerol 4 mL.

The components were dissolved and autoclaved; and the components were cooled to 60° C., and then added with 100 mL of sterilized 0.17 mol/L $KH_2PO_4$ and 0.72 mol/L $K_2HPO_4$ solution (2.31 g of $KH_2PO_4$ and 12.54 g of $K_2HPO_4$ were dissolved in sufficient water such that the final volume is 100 mL; filtration is performed by a 0.22 μm filter membrane for sterilization);

Culture Methods:

Seed culture: inoculating a single colony of engineering bacteria into a triangular flask (250 mL) with a liquid volume of 25 mL, and culturing at 37° C. at the shaking speed of 200 r/min for 12 h; and fermentation culture: inoculating into a triangular flask (250 mL) with a liquid volume of 25 mL according to the inoculation amount of 3%, culturing at 37° C., when $OD_{600}$ reached 0.6, adding IPTG for induction (wherein the induction amount of PGL, LOX, and ASN were respectively 0.04 mM, 1 mM and 1 mM) and adjusting the temperature to the optimum induction temperature of the enzyme, and culturing (PGL at 30° C. for 48 h, LOX at 20° C. for 24 h and ASN at 30° C. for 12 h).

Preparation of Protein Purification Liquid:

Buffer A: 20 mM phosphate buffer, 500 mM NaCl, 20 mM imidazole.

Buffer B: 20 mM phosphate buffer, 500 mM NaCl, 500M imidazole.

Preparation method of 20 mM pH7.4 phosphate buffer: adding 810 mL of 20 mM $Na_2HPO_4$ to 190 mL of 20 mM $NaH_2PO_4$.

Determination of Enzyme Activity and Heat Stability of Alkaline Pectinase:

Spectrophotometry was used for determination. Definition of unit enzyme activity: the amount of enzyme used to pyrolyze polygalacturonic acid to produce 1 μmol of unsaturated polygalacturonic acid per unit time. The enzyme activity determination conditions were: enzyme activity detection: the fermentation liquid was centrifuged at 8000 rpm for 10 min such that the extracellular PGL was contained in the fermentation supernatant, and a certain amount was taken for detection. PGL reaction system: 2 mL of glycine-NaOH buffer (0.2 mol/L, 0.44 mmol/L $CaCl_2$, pH9.4) containing 0.2% of polygalacturonic acid (substrate), 20 μL of a sample to be detected, and an inactive enzyme solution as a blank control. PGL reaction conditions: the reaction system was placed in a water bath at 45° C. for 15 min, the reaction was terminated with 3 mL of phosphoric acid solution (0.03 mol/L), and the absorbance was determined at 235 nm.

The diluted enzyme solution was dispensed and placed in a metal bath at 60° C., and the residual enzyme activity was measured every 3 minutes to calculate the half life.

Determination of Enzyme Activity and Heat Stability of Lipoxygenase:

The LOX enzyme activity was determined by spectrophotometry. 1 unit of LOX enzyme activity is defined as: the amount of enzyme required to catalyze the substrate linoleic acid to form 1 μmol of linoleic acid hydroperoxide (HPOD optical rotation coefficient=25000 L/(mol×cm) per minute at 25° C. Enzyme activity determination conditions: by using linoleic acid used as a substrate, the change in absorbance at 234 nm was measured on line at 25° C. by using a Shimadzu UV-2450 spectrophotometer, and the enzyme activity was calculated based on the slope of the initial portion of the absorbance change curve.

The purified enzyme was diluted with the buffer A to a protein concentration of 100 μg/mL and held at 50° C., and the residual enzyme activity was measured at intervals to calculate the half life.

Determination of Enzyme Activity and Heat Stability of Asparaginase:

The enzyme activity of ASN was determined by a Nessler's reagent method. (1) Enzymatic reaction: 1 mL of phosphate buffer (10 mmol/L, pH 7.5), 300 μL of enzyme solution, and 100 μL of substrate reacted at 37° C. for 30 min, and then the reaction was terminated by adding 100 μL of trichloroacetic acid; and the system was uniformly mixed, and centrifuged at 12000 r/min for 2 min. (2) Color reaction: 200 μL of enzymatic reaction solution in the first step, 3.3 mL of deionized water and 500 μL of Nessler's reagent were uniformly mixed, and the absorbance was determined at 436 nm.

Definition of enzyme activity unit: the amount of enzyme required to hydrolyze L-asparagine to produce 1 μmol of ammonia per minute is defined as an ASN activity unit.

Drawing of standard curve: a 18 mmol/L $(NH_4)_2SO_4$ standard solution was prepared, 0 μL, 50 μL, 100 μL, 200 μL, 250 μL, 300 μL, 350 μL and 400 μL of $(NH_4)_2SO_4$ were respectively added into a 1.5 mL tube and supplemented to 400 μL with deionized water, 1 mL of phosphate buffer (10 mmol/L, pH 7.5) was added to react at 37° C. for 30 min, 100 μL of trichloroacetic acid was added to terminate the reaction, and the system was uniformly mixed and centrifuged at 12000 r/min for 2 min, and then subjected to color reaction.

The diluted enzyme solution was dispensed and placed in a metal bath at 55° C., and the residual enzyme activity was measured every 3 minutes to calculate the half-life.

In this embodiment, a contrast group of PGL, LOX and ASN, and three implementation groups of SL1-PGL, SL2-PGL and SL3-PGL, SL1-LOX, SL2-LOX and SL3-LOX and SL1-ASN, SL2-ASN and SL3-ASN were set.

The construction and screening process of the functional polypeptide library involved in this embodiment is shown in FIG. 1. Analysis of characterization of the mutation rate of the functional polypeptide library involved is shown in FIGS. 2-7. The amino acid sequences of the SAP and linker are shown in Table 2.

TABLE 2

SAP and linker sequences

| Enzymes | SAP Sequence | Linker Sequence |
|---|---|---|
| PGL | | |
| SL1-PGL | SEQ ID NO.71 | SEQ ID NO.12 |
| SL2-PGL | SEQ ID NO.72 | SEQ ID NO.12 |
| SL3-PGL | SEQ ID NO.73 | SEQ ID NO.66 |
| LOX | | |
| SL1-LOX | SEQ ID NO.74 | SEQ ID NO.12 |
| SL2-LOX | SEQ ID NO.75 | SEQ ID NO.39 |
| SL3-LOX | SEQ ID NO.76 | SEQ ID NO.80 |
| ASN | | |
| SL1-ASN | SEQ ID NO.77 | SEQ ID NO.12 |
| SL2-ASN | SEQ ID NO.78 | SEQ ID NO.14 |
| SL3-ASN | SEQ ID NO.79 | SEQ ID NO.21 |

Example 1: Construction of Functional Polypeptide Library

According to the amino acid sequence 9S1(AEAEAKA-KAEAEAKAK)$_9$ of the amphipathic peptide, the gene was chemically synthesized, linked to the N-terminal of the gene sequence of the corresponding to-be-screened enzymes (PGL, LOX and ASN) and cloned between NdeI and NcoI restriction enzyme cutting sites of the plasmid pET-22b(+)/enzyme (enzyme is the to-be-screened protein expression gene, and is PGL, LOX and ASN here) of the target enzyme or protein to construct a pET-22b(+)/9S1-enzyme plasmid. The GFP expression gene gfp was fused at the pET-22b(+)/9S1-enzyme terminal to construct the pET-22b(+)/9S1-enzyme-gfp plasmid.

By using pET-22b(+)/9S1-enzyme-gfp plasmid as a template, a degenerate forward primer nSAP-up and a specific reverse primer nSAP-down$_{enzyme}$ were subjected to PCR to obtain the linearized pET-22b(+)/nSAP-enzyme-gfp linearized gene segment containing SAPs of different amino acid compositions and lengths.

The linker gene was previously chemically synthesized and linked to a pMD18-T vector, and PCR was performed by using universal forward LR-up and LF-up and specific reverse LR-down$_{enzyme}$ and LF-down$_{enzyme}$ as primers to obtain the linker gene segment. The linker gene segment and the linearized pET-22b(+)/nSAP-enzyme-gfp gene segment were subjected to homologous recombination to obtain the pET-22b(+)/nSAP-linker-enzyme-gfp mixed plasmid (Relevant primers are shown in table 3).

TABLE 3

Primer

| Primers | Sequence (5'-3') | Notes |
|---|---|---|
| pgl-up | SEQ ID NO.81 | |
| pgl-down | SEQ ID NO.82 | |
| lox-up | SEQ ID NO.83 | |
| lox-down | SEQ ID NO.84 | |
| asn-up | SEQ ID NO.85 | |
| asn-down | SEQ ID NO.86 | |
| nS1-up | SEQ ID NO.87 | constant |
| nS1-down$_{pgl}$ | SEQ ID NO.88 | specific for PGL |
| nS1-down$_{lox}$ | SEQ ID NO.89 | specific for LOX |
| nS1-down$_{asn}$ | SEQ ID NO.90 | specific for ASN |
| L-up$_R$ | SEQ ID NO.91 | constant |
| L-up$_F$ | SEQ ID NO.92 | constant |
| L-down$_R$ | SEQ ID NO.93 | specific for PGL |

TABLE 3-continued

| Primers | Sequence (5'-3') | Notes |
|---|---|---|
| L-down$_R$ | SEQ ID NO.94 | specific for LOX |
| L-down$_R$ | SEQ ID NO.95 | specific for ASN |
| L-down$_F$ | SEQ ID NO.96 | specific for PGL |
| L-down$_F$ | SEQ ID NO.97 | specific for LOX |
| L-down$_F$ | SEQ ID NO.98 | specific for ASN |

Example 2: Preliminary Screening

Preliminary screening: the recombinant plasmid and recombinant plasmid library were transformed to an expression host E. coli BL21(DE3), cultured in a seed medium and subjected to induction, and cultured for some time (based on the expression condition of the to-be-screened enzyme), (the related culture method: when OD$_{600}$ reached 0.6, adding IPTG for induction (wherein the IPTG induction amount of PGL-GFP fusion enzyme, LOX-GFP, and ASN-GFP were respectively 0.04 mM, 1 mM and 1 mM) and adjusting the temperature to the optimum induction temperature of the enzyme, and culturing (PGL-GFP at 30° C. for 5, LOX-GFP at 20° C. for 10 h and ASN-GFP at 30° C. for 5 h).). The to-be-screened cells were diluted, and the sample was subjected to analysis and testing by using the following detection parameters: the jet size of the MoFlo XDP flow cytometry (Beckman Coulter, USA) was set to 100 μm, 20 mM of pH7.4 phosphate buffer was used as sheath fluid, cell OD$_{600}$ was set to 0.1 or below, the cell flow rate was 5000 particles/second, the wavelength of excitation light was 488 nm, and the wavelength of emitted light was 530/40 nm. The corresponding blank control was deducted.

Example 3: Re-Screening and Identification

Re-screening and identification: The mutant with high fluorescence intensity obtained after screening by the flow cytometry was subjected to shake flask culture and fluorescence intensity determination. A single colony was inoculated into a seed medium, cultured over night and transformed into a fermentation medium; and when OD$_{600}$ reached 0.6, IPTG was added for induction (wherein the IPTG induction amount of PGL-GFP fusion enzyme, LOX-GFP, and ASN-GFP were respectively 0.04 mM and 1 mM), the temperature was adjusted to the optimum induction temperature of the enzyme, and culture was performed (PGL-GFP at 30° C. for 48 h, LOX-GFP at 20° C. for 72 h and ASN-GFP at 30° C. for 24 h).

Example 4: Fluorescent Protein Gene Deletion

GFP gene deletion was performed by using the above obtained high-expression mutant plasmid as the template, and the primers are shown in Table 2.

Example 5: Enzyme Mutant Detection

Recombinant bacterium fermentation culture: a seed medium was cultured at 37° C. over night and transformed into a fermentation medium; and when OD$_{600}$ reached 0.6, IPTG was added for induction (wherein the IPTG induction amount of PGL fusion enzyme, LOX 1 mM, and ASN were respectively 0.04 mM, 1 mM and 1 mM), the temperature was adjusted to the optimum induction temperature of the enzyme, and culture was performed (PGL at 30° C. for 48 h, LOX at 20° C. for 72 h and ASN at 30° C. for 24 h). The recombinant enzyme was appropriately diluted in a 96-well plate; and the PGL recombinase was placed at 65° C., the LOX recombinase was placed at 55° C., and the ASN recombinase was placed at 70° C. for heat treatment to determine the residual enzyme activity. The detection results are shown in Table 4.

TABLE 4

Expression level and property characterization of fusion enzyme mutants

| Enzymes | Crude Enzyme Activity (U/mL) | Half Life (min) | Specific Enzyme Activity (U/mg) |
|---|---|---|---|
| PGL | 131.17 ± 2.4 | 5.2 ± 0.22 | 264.17 ± 5.2 |
| SL1PGL | 2140.42 ± 6.7 | 21.25 ± 0.93 | 918.72 ± 8.4 |
| SL2PGL | 2033.9 ± 9.1 | 25.29 ± 1.1 | 937.18 ± 5.4 |
| SL3PGL | 1432.6 ± 7.4 | 15.2 ± 0.3 | 710.2 ± 5.7 |
| LOX | 1.54 ± 0.02 | 10.2 ± 0.2 | 30.2 ± 0.97 |
| SL1LOX | 5.38 ± 0.03 | 18.2 ± 0.5 | 42.7 ± 1.5 |
| SL2LOX | 2.77 ± 0.02 | 42.2 ± 0.9 | 26.21 ± 0.13 |
| SL3LOX | 3.08 ± 0.04 | 30.6 ± 0.7 | 57.6 ± 1.2 |
| ASN | 3.8 ± 0.06 | 12.3 ± 0.42 | 17.24 ± 0.23 |
| SL1ASN | 12.36 ± 0.18 | 56.21 ± 1.1 | 19.21 ± 0.44 |
| SL2ASN | 7.12 ± 0.2 | 27.18 ± 0.4 | 15.29 ± 0.8 |
| SL3ASN | 5.3 ± 0.6 | 24.4 ± 0.17 | 40.4 ± 1.88 |

Example 6: Enzyme Mutant Purification

Purification Method of Alkaline Pectinase:

The fermentation supernatant was centrifuged at 9000 r/min for 15 min to obtain a fermentation supernatant containing alkaline pectinase. The fermentation liquid was subjected to preliminary concentration by ammonium sulfate precipitation on ice. After dialysis and desalting, the sample was filtered through a 0.22 μm microporous filter membrane and separated and purified by using a 5 mL cation exchange chromatography column (HiTrap™ SP FF, GE). Purification conditions: 10-15 times of column volume of buffer A (20 mmol/L glycine-sodium hydroxide buffer, pH 7.4) was used for balancing the hydrophobic interaction column at the flow rate of 2 mL/min, 5 mL of sample was introduced at the flow rate of 1 mL/min, the buffer A was introduced again at the flow rate of 2 mL/min for balancing until the curve became stable, and linear elution was performed with the buffer B (20 mmol/L glycine-sodium hydroxide buffer, 1 mol/L NaCl, pH 7.4). The obtained PGL-containing eluate was dialyzed and desalted in the buffer A, and stored at 4° C.

Purification Method of Lipoxygenase:

The fermentation supernatant was centrifuged at 9000 r/min for 15 min to obtain a fermentation supernatant containing alkaline pectinase and 10% (w/v) glycerol was added, ground and dried ammonium sulfate powder was slowly added until the saturation degree of the ammonium sulfate was 40%, and stirring was slowly performed for 30 min; and the sample was then centrifuged at 12000 rpm for 15 min, the precipitate was collected and redissolved in the buffer A containing 50 mmol/L NaCl, and the precipitate was removed by centrifugation to obtain the supernatant, which was the ammonium sulfate precipitated sample.

The ammonium sulfate precipitated sample was dialyzed in the buffer A containing 50 mmol/L NaCl in a dialysis bag with the molecular weight cut off of 50 kDa for 24 h, and then dialyzed in the buffer A for 24 h for desalting.

The Histrap1mLFF purification column was balanced with the buffer A at the flow rate of 1 mL/min, then loaded, balanced, and was linearly eluted with the buffer B to collect the component of the recombinant LOX. The obtained LOX-containing eluate was dialyzed and desalted in the buffer A, and stored at 4° C.

Purification Method of Asparaginase:

The fermentation supernatant was centrifuged at 9000 r/min for 15 min to obtain a fermentation supernatant containing alkaline pectinase. The fermentation liquid was subjected to preliminary concentration by ammonium sulfate precipitation on ice. After dialysis and desalting, the sample was filtered through a 0.22 μm microporous filter membrane, redissolved with the buffer A and separated and purified by using a 5 mL hydrophobic chromatographic column (HiTrap™ SP FF, GE). Purification conditions: 10-15 times of column volume of buffer A (20 mmol/L glycine-sodium hydroxide buffer, pH 7.4) was used for balancing the hydrophobic interaction column at the flow rate of 2 mL/min, 5 mL of sample was introduced at the flow rate of 1 mL/min, the buffer A was introduced again at the flow rate of 2 mL/min for balancing until the curve became stable, and linear elution was performed with the buffer B (20 mmol/L glycine-sodium hydroxide buffer, 1 mol/L NaCl, pH 7.4). The obtained ASN-containing eluate was dialyzed and desalted in the buffer A, and stored at 4° C.

What is claimed is:

1. An asparaginase mutant, wherein the amino acid sequence of the asparaginase mutant is set forth in SEQ ID NO: 99, SEQ ID NO: 100, or SEQ ID NO: 101.

2. A gene encoding the asparaginase mutant of claim 1.

3. A recombinant plasmid comprising the gene of claim 2.

4. The recombinant plasmid of claim 3, wherein the recombinant plasmid is constructed from a pUC, pET or pGEX.

5. The recombinant plasmid of claim 3, wherein the recombinant plasmid is constructed from a pET.

6. A host cell comprising the gene of claim 2.

7. A host cell comprising the recombinant plasmid of claim 3.

8. A method, wherein the method comprises expressing the asparaginase mutant of claim 1 at a predetermined condition.

* * * * *

SEQUENCE LISTING

```
<160> NUMBER OF SEQ ID NOS: 101

<210> SEQ ID NO 1
<211> LENGTH: 432
<212> TYPE: DNA
<213> ORGANISM: Artificial Sequence
<220> FEATURE:
<223> OTHER INFORMATION: Synthetic DNA

<400> SEQUENCE: 1
gcagaagcag aagcgaaagc caaagcggag gcggaagcca aggctaaagc agaagcagaa     60
gcgaaagcca aagcggaggc ggaagccaag gctaaagcag aagcagaagc gaaagccaaa    120
gcggaggcgg aagccaaggc taaagcagaa gcagaagcga agccaaagc ggaggcggaa    180 gccaaggcta aagcagaagc agaagcgaaa gccaaagcgg aggcggaagc caaggctaaa    240
gcagaagcag aagcgaaagc caaagcggag gcggaagcca aggctaaagc agaagcagaa    300
gcgaaagcca aagcggaggc ggaagccaag gctaaagcag aagcagaagc gaaagccaaa    360
gcggaggcgg aagccaaggc taaagcagaa gcagaagcga aagccaaagc ggaggcggaa    420
gccaaggcta aa                                                        432

<210> SEQ ID NO 2
<211> LENGTH: 5
<212> TYPE: PRT
<213> ORGANISM: Artificial Sequence
<220> FEATURE:
<223> OTHER INFORMATION: Protein translated from synthetic DNA

<400> SEQUENCE: 2

Glu Ala Ala Ala Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Protein translated from synthetic DNA

<400> SEQUENCE: 3

Gly Gly Gly Gly Ser
1               5

<210> SEQ ID NO 4
<211> LENGTH: 15
<212> TYPE: DNA
<213> ORGANISM: Artificial Sequence
<220> FEATURE:
<223> OTHER INFORMATION: Synthetic DNA
```

```
<400> SEQUENCE: 4
gaagctgcgg caaaa                                                      15

<210> SEQ ID NO 5
<211> LENGTH: 15
<212> TYPE: DNA
<213> ORGANISM: Artificial Sequence
<220> FEATURE:
<223> OTHER INFORMATION: Synthetic DNA

<400> SEQUENCE: 5
ggtggtggcg gttcg                                                      15

<210> SEQ ID NO 6
<211> LENGTH: 401
<212> TYPE: PRT
<213> ORGANISM: Artificial Sequence
<220> FEATURE:
<223> OTHER INFORMATION: Protein translated from synthetic DNA

<400> SEQUENCE: 6
```

Met Asp Ala Asp Leu Gly His Gln Thr Leu Gly Ser Asn Asp Gly Trp
1               5                   10                  15

Gly Ala Tyr Ser Thr Gly Thr Thr Gly Gly Ser Lys Ala Ser Ser Leu
            20                  25                  30

Asn Val Tyr Thr Val Ser Asn Arg Asn Gln Leu Val Ser Ala Leu Gly
        35                  40                  45

Lys Glu Thr Asn Thr Thr Pro Lys Ile Ile Tyr Ile Lys Gly Thr Ile
    50                  55                  60

Asp Met Asn Val Asp Asp Asn Leu Lys Pro Leu Gly Leu Asn Asp Tyr
65                  70                  75                  80

Lys Asp Pro Glu Tyr Asp Leu Asp Lys Tyr Leu Lys Ala Tyr Asp Pro
                85                  90                  95

Ser Thr Trp Gly Lys Lys Glu Pro Ser Gly Thr Gln Glu Glu Ala Arg
            100                 105                 110

Ala Arg Ser Gln Lys Asn Gln Lys Ala Arg Val Met Val Asp Ile Pro
        115                 120                 125

Ala Asn Thr Thr Ile Val Gly Ser Gly Thr Asn Ala Lys Val Val Gly
    130                 135                 140

Gly Asn Phe Gln Ile Lys Ser Asp Asn Val Ile Ile Arg Asn Ile Glu
145                 150                 155                 160

Phe Gln Asp Ala Tyr Asp Tyr Phe Pro Gln Trp Asp Pro Thr Asp Gly
                165                 170                 175

Ser Ser Gly Asn Trp Asn Ser Gln Tyr Asp Asn Ile Thr Ile Asn Gly
            180                 185                 190

Gly Thr His Ile Trp Ile Asp His Cys Thr Phe Asn Asp Gly Ser Arg
        195                 200                 205

Pro Asp Ser Thr Ser Pro Lys Tyr Tyr Gly Arg Lys Tyr Gln His His
    210                 215                 220

Asp Gly Gln Thr Asp Ala Ser Asn Gly Ala Asn Tyr Ile Thr Met Ser
225                 230                 235                 240

Tyr Asn Tyr Tyr His Asp His Asp Lys Ser Ser Ile Phe Gly Ser Ser
                245                 250                 255

Asp Ser Lys Thr Ser Asp Asp Gly Lys Leu Lys Ile Thr Leu His His
            260                 265                 270

Asn Arg Tyr Lys Asn Ile Val Gln Arg Ala Pro Arg Val Arg Phe Gly
        275                 280                 285

```
Gln Val His Val Tyr Asn Asn Tyr Tyr Glu Gly Ser Thr Ser Ser Ser
    290                 295                 300
Ser Tyr Pro Phe Ser Tyr Ala Trp Gly Ile Gly Lys Ser Ser Lys Ile
305                 310                 315                 320
Tyr Ala Gln Asn Asn Val Ile Asp Val Pro Gly Leu Ser Ala Ala Lys
                325                 330                 335
Thr Ile Ser Val Phe Ser Gly Gly Thr Ala Leu Tyr Asp Ser Gly Thr
            340                 345                 350
Leu Leu Asn Gly Thr Gln Ile Asn Ala Ser Ala Ala Asn Gly Leu Ser
        355                 360                 365
Ser Ser Val Gly Trp Thr Pro Ser Leu His Gly Ser Ile Asp Ala Ser
    370                 375                 380
Ala Asn Val Lys Ser Asn Val Ile Asn Gln Ala Gly Ala Gly Lys Leu
385                 390                 395                 400
Asn

<210> SEQ ID NO 7
<211> LENGTH: 667
<212> TYPE: PRT
<213> ORGANISM: Artificial Sequence
<220> FEATURE:
<223> OTHER INFORMATION: Protein translated from synthetic DNA

<400> SEQUENCE: 7

Met Asn Asp Ser Ile Phe Phe Ser Pro Leu Lys Tyr Leu Gly Ala Glu
1               5                   10                  15
Gln Gln Arg Ser Ile Asp Ala Ser Arg Ser Leu Leu Asp Asn Leu Ile
            20                  25                  30
Pro Pro Ser Leu Pro Gln Tyr Asp Asn Leu Ala Gly Lys Leu Ala Arg
        35                  40                  45
Arg Ala Val Leu Thr Ser Lys Lys Leu Val Tyr Val Trp Thr Glu Asn
    50                  55                  60
Phe Gly Asn Val Lys Gly Val Pro Met Ala Arg Ser Val Pro Leu Gly
65                  70                  75                  80
Glu Leu Pro Asn Val Asp Trp Leu Leu Lys Thr Ala Gly Val Ile Val
            85                  90                  95
Glu Leu Ile Val Asn Phe Val Ala Ser Leu Pro Ala Ser Ala Ala Ala
            100                 105                 110
Gln Phe Glu Arg Ile Ala Thr Gly Leu Ser Gly Asp Leu Glu Ala Ala
        115                 120                 125
Arg Gln Val His Glu Ala Leu Leu Glu Ala Lys Asn Asp Pro Ala
    130                 135                 140
Ala Ala Gly Ser Leu Leu Leu Arg Phe Thr Glu Leu Gln Thr Arg Val
145                 150                 155                 160
Ile Ala Ile Leu Thr Arg Val Gly Leu Val Asp Asp Ile Leu Lys
                165                 170                 175
Ser Ala Ser Asn Leu Val Thr Gln Arg Gly Gln Gly Asp Gly Leu Asn
            180                 185                 190
Arg Phe Arg Ala Val Phe Gly Thr Leu Arg Leu Pro Glu Val Ala Asp
        195                 200                 205
Ser Phe Arg Asp Asp Glu Ala Phe Ala Tyr Trp Arg Val Ala Gly Pro
    210                 215                 220
Asn Pro Leu Leu Ile Arg Arg Val Asp Ala Leu Pro Ala Asn Phe Pro
225                 230                 235                 240
```

```
Leu Gly Glu Glu Gln Phe Arg Arg Val Met Gly Ala Asp Asp Ser Leu
                245                 250                 255

Leu Glu Ala Ala Ala Ser Arg Arg Leu Tyr Leu Leu Asp Tyr Ala Glu
                260                 265                 270

Leu Gly Lys Leu Ala Pro Ser Gly Ala Val Asp Lys Leu Leu Thr Gly
                275                 280                 285

Thr Gly Phe Ala Tyr Ala Pro Ile Ala Leu Phe Ala Leu Gly Lys Asp
                290                 295                 300

Arg Ala Arg Leu Leu Pro Val Ala Ile Gln Cys Gly Gln Asp Pro Ala
305                 310                 315                 320

Thr His Pro Met Phe Val Arg Pro Ala Glu Ser Glu Ser Asp Leu Tyr
                325                 330                 335

Trp Gly Trp Gln Met Ala Lys Thr Val Val Gln Val Ala Glu Glu Asn
                340                 345                 350

Tyr His Glu Met Phe Val His Leu Ala Gln Thr His Leu Val Ser Glu
                355                 360                 365

Ala Phe Cys Leu Ala Thr Gln Arg Thr Leu Ala Pro Ser His Pro Leu
                370                 375                 380

His Val Leu Leu Ala Pro His Phe Glu Gly Thr Leu Phe Ile Asn Glu
385                 390                 395                 400

Gly Ala Ala Arg Ile Leu Leu Pro Ser Ala Gly Phe Ile Asp Val Met
                405                 410                 415

Phe Ala Ala Pro Ile Gln Asp Thr Gln Ala Thr Ala Gly Gly Asn Arg
                420                 425                 430

Leu Gly Phe Asp Phe Tyr Arg Gly Met Leu Pro Glu Ser Leu Lys Ala
                435                 440                 445

Arg Asn Val Asp Asp Pro Leu Ala Leu Pro Asp Tyr Pro Tyr Arg Asp
450                 455                 460

Asp Gly Leu Leu Val Trp Asn Ala Ile Arg Gln Trp Ala Ala Asp Tyr
465                 470                 475                 480

Val Ala Val Tyr Tyr Ala Ser Asp Gly Asp Val Thr Ala Asp Val Glu
                485                 490                 495

Leu Ala Ala Trp Val Gly Glu Val Ile Gly Ser Gly Lys Val Ala Gly
                500                 505                 510

Phe Arg Pro Ile Thr Gly Arg Ser Gln Leu Val Glu Val Leu Thr Met
                515                 520                 525

Val Ile Phe Thr Ala Ser Ala Gln His Ala Ala Val Asn Phe Pro Gln
                530                 535                 540

Pro Ser Met Met Thr Tyr Ala Pro Ala Ile Cys Ala Met Ser Ala Ala
545                 550                 555                 560

Pro Ala Pro Asp Ser Pro Ser Gly Lys Ser Glu Ala Asp Trp Leu Lys
                565                 570                 575

Met Met Pro Pro Thr Leu Val Ala Leu Glu Lys Val Asn Ile Tyr His
                580                 585                 590

Leu Leu Gly Ser Val Tyr His Gly Arg Leu Gly Asp Tyr Arg Gln Thr
                595                 600                 605

Gly Phe Pro Tyr Ala Pro Val Phe Ser Asp Arg Val Thr Ala Ser
                610                 615                 620

Gly Gly Pro Leu Glu Arg Phe Gln Ala Arg Leu Lys Glu Val Glu Ala
625                 630                 635                 640

Thr Ile Arg Thr Arg Asn Gln Ala Arg Arg Pro Tyr Glu Tyr Leu
                645                 650                 655

Leu Pro Ser Arg Ile Pro Ala Ser Thr Asn Ile
```

<210> SEQ ID NO 8
<211> LENGTH: 370
<212> TYPE: PRT
<213> ORGANISM: Artificial Sequence
<220> FEATURE:
<223> OTHER INFORMATION: Protein translated from synthetic DNA

<400> SEQUENCE: 8

```
Met Lys Tyr Leu Leu Pro Thr Ala Ala Ala Gly Leu Leu Leu Leu Ala
  1               5                  10                  15

Ala Gln Pro Ala Met Ala Met Glu Phe Phe Lys Lys Thr Ala Leu Ala
             20                  25                  30

Ala Leu Val Met Gly Phe Ser Gly Ala Ala Leu Ala Leu Pro Asn Ile
         35                  40                  45

Thr Ile Leu Ala Thr Gly Gly Thr Ile Ala Gly Gly Gly Asp Ser Ala
     50                  55                  60

Thr Lys Ser Asn Tyr Thr Ala Gly Lys Val Gly Val Glu Asn Leu Val
 65                  70                  75                  80

Asn Ala Val Pro Gln Leu Lys Asp Ile Ala Asn Val Lys Gly Glu Gln
                 85                  90                  95

Val Val Asn Ile Gly Ser Gln Asp Met Asn Asp Asp Val Trp Leu Thr
            100                 105                 110

Leu Ala Lys Lys Ile Asn Thr Asp Cys Asp Lys Thr Asp Gly Phe Val
        115                 120                 125

Ile Thr His Gly Thr Asp Thr Met Glu Glu Thr Ala Tyr Phe Leu Asp
    130                 135                 140

Leu Thr Val Lys Cys Asp Lys Pro Val Val Met Val Gly Ala Met Arg
145                 150                 155                 160

Pro Ser Thr Ser Met Ser Ala Asp Gly Pro Phe Asn Leu Tyr Asn Ala
                165                 170                 175

Val Val Thr Ala Ala Asp Lys Ala Ser Ala Asn Arg Gly Val Leu Val
            180                 185                 190

Val Met Asn Asp Thr Val Leu Asp Gly Arg Asp Val Thr Lys Thr Asn
        195                 200                 205

Thr Thr Asp Val Ala Thr Phe Lys Ser Val Asn Tyr Gly Pro Leu Gly
    210                 215                 220

Tyr Ile His Asn Gly Lys Ile Asp Tyr Gln Arg Thr Pro Ala Arg Lys
225                 230                 235                 240

His Thr Ser Asp Thr Pro Phe Asp Val Ser Lys Leu Asn Glu Leu Pro
                245                 250                 255

Lys Val Gly Ile Val Tyr Asn Tyr Ala Asn Ala Ser Asp Leu Pro Ala
            260                 265                 270

Lys Ala Leu Val Asp Ala Gly Tyr Asp Gly Ile Val Ser Ala Gly Val
        275                 280                 285

Gly Asn Gly Asn Leu Tyr Lys Thr Val Phe Asp Thr Leu Ala Thr Ala
    290                 295                 300

Ala Lys Asn Gly Thr Ala Val Val Arg Ser Ser Arg Val Pro Thr Gly
305                 310                 315                 320

Ala Thr Thr Gln Asp Ala Glu Val Asp Asp Ala Lys Tyr Gly Phe Val
                325                 330                 335

Ala Ser Gly Thr Leu Asn Pro Gln Lys Ala Arg Val Leu Leu Gln Leu
            340                 345                 350

Val Leu Thr Gln Thr Lys Asp Pro Gln Gln Ile Gln Gln Ile Phe Asn
```

```
            355                 360                 365

Gln Tyr
    370

<210> SEQ ID NO 9
<211> LENGTH: 5
<212> TYPE: PRT
<213> ORGANISM: Artificial Sequence
<220> FEATURE:
<223> OTHER INFORMATION: Protein translated from synthetic DNA

<400> SEQUENCE: 9

Glu Ala Ala Ala Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Protein translated from synthetic DNA

<400> SEQUENCE: 10

Gly Gly Gly Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Protein translated from synthetic DNA

<400> SEQUENCE: 11

Glu Ala Ala Ala Lys Glu Ala Ala Ala Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Protein translated from synthetic DNA

<400> SEQUENCE: 12

Gly Gly Gly Gly Ser Gly Gly Gly Gly Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Protein translated from synthetic DNA

<400> SEQUENCE: 13

Glu Ala Ala Ala Lys Gly Gly Gly Gly Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Protein translated from synthetic DNA

<400> SEQUENCE: 14
```

Gly Gly Gly Gly Ser Glu Ala Ala Ala Lys
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 15

Glu Ala Ala Ala Lys Glu Ala Ala Ala Lys Glu Ala Ala Ala Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 17

Glu Ala Ala Ala Lys Glu Ala Ala Ala Lys Gly Gly Gly Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 18

Gly Gly Gly Gly Ser Gly Gly Gly Gly Ser Glu Ala Ala Ala Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 19

Glu Ala Ala Ala Lys Gly Gly Gly Gly Ser Gly Gly Gly Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 20

```
Gly Gly Gly Gly Ser Glu Ala Ala Ala Lys Glu Ala Ala Ala Lys
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 21

```
Glu Ala Ala Ala Lys Gly Gly Gly Gly Ser Glu Ala Ala Ala Lys
1               5                   10                  15
```

<210> SEQ ID NO 22
<211> LENGTH: 15
<212> TYPE: PRT
<213> ORGANISM: Artificial Sequence
<220> FEATURE:
<223> OTHER INFORMATION: Protein translated from synthetic DNA

<400> SEQUENCE: 22

```
Gly Gly Gly Gly Ser Glu Ala Ala Ala Lys Gly Gly Gly Gly Ser
1               5                   10                  15
```

<210> SEQ ID NO 23
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 23

```
Glu Ala Ala Ala Lys Glu Ala Ala Ala Lys Glu Ala Ala Ala Lys Glu
1               5                   10                  15

Ala Ala Ala Lys
            20
```

<210> SEQ ID NO 24
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 24

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 25
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 25

```
Glu Ala Ala Ala Lys Glu Ala Ala Ala Lys Glu Ala Ala Ala Lys Gly
1               5                   10                  15

Gly Gly Gly Ser
            20
```

<210> SEQ ID NO 26

```
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 26

Gly Gly Gly Gly Ser Gly Gly Gly Gly Ser Gly Gly Gly Ser Glu
1               5                   10                  15

Ala Ala Ala Lys
            20

<210> SEQ ID NO 27
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 27

Glu Ala Ala Ala Lys Glu Ala Ala Ala Lys Gly Gly Gly Gly Ser Gly
1               5                   10                  15

Gly Gly Gly Ser
            20

<210> SEQ ID NO 28
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 28

Gly Gly Gly Gly Ser Gly Gly Gly Gly Ser Glu Ala Ala Ala Lys Glu
1               5                   10                  15

Ala Ala Ala Lys
            20

<210> SEQ ID NO 29
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 29

Glu Ala Ala Ala Lys Gly Gly Gly Gly Ser Gly Gly Gly Gly Ser Gly
1               5                   10                  15

Gly Gly Gly Ser
            20

<210> SEQ ID NO 30
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 30

Gly Gly Gly Gly Ser Glu Ala Ala Ala Lys Glu Ala Ala Ala Lys Glu
1               5                   10                  15

Ala Ala Ala Lys
            20
```

```
<210> SEQ ID NO 31
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 31

Glu Ala Ala Ala Lys Gly Gly Gly Gly Ser Gly Gly Gly Gly Ser Glu
1               5                   10                  15

Ala Ala Ala Lys
            20

<210> SEQ ID NO 32
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 32

Gly Gly Gly Gly Ser Glu Ala Ala Ala Lys Glu Ala Ala Ala Lys Gly
1               5                   10                  15

Gly Gly Gly Ser
            20

<210> SEQ ID NO 33
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 33

Glu Ala Ala Ala Lys Gly Gly Gly Gly Ser Glu Ala Ala Ala Lys Gly
1               5                   10                  15

Gly Gly Gly Ser
            20

<210> SEQ ID NO 34
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 34

Gly Gly Gly Gly Ser Glu Ala Ala Ala Lys Gly Gly Gly Gly Ser Glu
1               5                   10                  15

Ala Ala Ala Lys
            20

<210> SEQ ID NO 35
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 35

Glu Ala Ala Ala Lys Gly Gly Gly Gly Ser Glu Ala Ala Ala Lys Glu
1               5                   10                  15

Ala Ala Ala Lys
            20
```

<210> SEQ ID NO 36
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 36

Gly Gly Gly Gly Ser Glu Ala Ala Ala Lys Gly Gly Gly Gly Ser Gly
1               5                   10                  15

Gly Gly Gly Ser
            20

<210> SEQ ID NO 37
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 37

Glu Ala Ala Ala Lys Glu Ala Ala Ala Lys Gly Gly Gly Gly Ser Glu
1               5                   10                  15

Ala Ala Ala Lys
            20

<210> SEQ ID NO 38
<211> LENGTH: 20
<212> TYPE: PRT
<213> ORGANISM: Artificial Sequence
<220> FEATURE:
<223> OTHER INFORMATION: Protein translated from synthetic DNA

<400> SEQUENCE: 38

Gly Gly Gly Gly Ser Gly Gly Gly Gly Ser Glu Ala Ala Ala Lys Gly
1               5                   10                  15

Gly Gly Gly Ser
            20

<210> SEQ ID NO 39
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 39

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 40
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 40

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 41
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 41

Glu Ala Ala Ala Lys Glu Ala Ala Ala Lys Glu Ala Ala Ala Lys Glu
1               5                   10                  15

Ala Ala Ala Lys Gly Gly Gly Gly Ser
            20                  25

<210> SEQ ID NO 42
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 42

Gly Gly Gly Gly Ser Gly Gly Gly Gly Ser Gly Gly Gly Gly Ser Gly
1               5                   10                  15

Gly Gly Gly Ser Glu Ala Ala Ala Lys
            20                  25

<210> SEQ ID NO 43
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 43

Glu Ala Ala Ala Lys Glu Ala Ala Ala Lys Glu Ala Ala Ala Lys Gly
1               5                   10                  15

Gly Gly Gly Ser Gly Gly Gly Gly Ser
            20                  25

<210> SEQ ID NO 44
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 44

Gly Gly Gly Gly Ser Gly Gly Gly Gly Ser Gly Gly Gly Gly Ser Glu
1               5                   10                  15

Ala Ala Ala Lys Glu Ala Ala Ala Lys
            20                  25

<210> SEQ ID NO 45
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 45

Glu Ala Ala Ala Lys Glu Ala Ala Ala Lys Gly Gly Gly Gly Ser Gly
1               5                   10                  15

Gly Gly Gly Ser Gly Gly Gly Gly Ser

-continued

```
                    20                  25

<210> SEQ ID NO 46
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 46

Gly Gly Gly Gly Ser Gly Gly Gly Gly Ser Glu Ala Ala Ala Lys Glu
1               5                   10                  15

Ala Ala Ala Lys Glu Ala Ala Ala Lys
            20                  25

<210> SEQ ID NO 47
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 47

Glu Ala Ala Ala Lys Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 48
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 48

Gly Gly Gly Gly Ser Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 49
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 49

Glu Ala Ala Ala Lys Gly Gly Gly Gly Ser Gly Gly Gly Gly Ser Gly
1               5                   10                  15

Gly Gly Gly Ser Glu Ala Ala Ala Lys
            20                  25

<210> SEQ ID NO 50
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 50

Gly Gly Gly Gly Ser Glu Ala Ala Ala Lys Glu Ala Ala Ala Lys Glu
1               5                   10                  15
```

Ala Ala Ala Lys Gly Gly Gly Gly Ser
            20                  25

<210> SEQ ID NO 51
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 51

Glu Ala Ala Ala Lys Gly Gly Gly Gly Ser Gly Gly Gly Gly Ser Glu
1               5                   10                  15

Ala Ala Ala Lys Gly Gly Gly Gly Ser
            20                  25

<210> SEQ ID NO 52
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 52

Gly Gly Gly Gly Ser Glu Ala Ala Ala Lys Glu Ala Ala Ala Lys Gly
1               5                   10                  15

Gly Gly Ser Glu Ala Ala Ala Lys
            20                  25

<210> SEQ ID NO 53
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 53

Glu Ala Ala Ala Lys Glu Ala Ala Ala Lys Gly Gly Gly Gly Ser Gly
1               5                   10                  15

Gly Gly Ser Glu Ala Ala Ala Lys
            20                  25

<210> SEQ ID NO 54
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 54

Gly Gly Gly Gly Ser Gly Gly Gly Ser Glu Ala Ala Ala Lys Glu
1               5                   10                  15

Ala Ala Ala Lys Gly Gly Gly Gly Ser
            20                  25

<210> SEQ ID NO 55
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 55

Glu Ala Ala Ala Lys Gly Gly Gly Gly Ser Gly Gly Gly Gly Ser Glu
1               5                   10                  15

Ala Ala Ala Lys Glu Ala Ala Ala Lys
            20                  25

<210> SEQ ID NO 56
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 56

Gly Gly Gly Gly Ser Glu Ala Ala Ala Lys Glu Ala Ala Ala Lys Gly
1               5                   10                  15

Gly Gly Gly Ser Gly Gly Gly Gly Ser
            20                  25

<210> SEQ ID NO 57
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 57

Glu Ala Ala Ala Lys Gly Gly Gly Gly Ser Glu Ala Ala Ala Lys Glu
1               5                   10                  15

Ala Ala Ala Lys Glu Ala Ala Ala Lys
            20                  25

<210> SEQ ID NO 58
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 58

Gly Gly Gly Gly Ser Glu Ala Ala Ala Lys Gly Gly Gly Gly Ser Gly
1               5                   10                  15

Gly Gly Gly Ser Gly Gly Gly Gly Ser
            20                  25

<210> SEQ ID NO 59
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 59

Glu Ala Ala Ala Lys Glu Ala Ala Ala Lys Gly Gly Gly Gly Ser Glu
1               5                   10                  15

Ala Ala Ala Lys Glu Ala Ala Ala Lys
            20                  25

<210> SEQ ID NO 60
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 60

Gly Gly Gly Gly Ser Gly Gly Gly Gly Ser Glu Ala Ala Ala Lys Gly

Gly Gly Gly Ser Gly Gly Gly Gly Ser
            20                  25

<210> SEQ ID NO 61
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 61

Glu Ala Ala Ala Lys Glu Ala Ala Ala Lys Glu Ala Ala Ala Lys Gly
1               5                   10                  15

Gly Gly Gly Ser Glu Ala Ala Ala Lys
            20                  25

<210> SEQ ID NO 62
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 62

Gly Gly Gly Gly Ser Gly Gly Gly Gly Ser Gly Gly Gly Gly Ser Glu
1               5                   10                  15

Ala Ala Ala Lys Gly Gly Gly Gly Ser
            20                  25

<210> SEQ ID NO 63
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 63

Glu Ala Ala Ala Lys Gly Gly Gly Gly Ser Glu Ala Ala Ala Lys Gly
1               5                   10                  15

Gly Gly Gly Ser Glu Ala Ala Ala Lys
            20                  25

<210> SEQ ID NO 64
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 64

Gly Gly Gly Gly Ser Glu Ala Ala Ala Lys Gly Gly Gly Gly Ser Glu
1               5                   10                  15

Ala Ala Ala Lys Gly Gly Gly Gly Ser
            20                  25

<210> SEQ ID NO 65
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 65

Glu Ala Ala Ala Lys Glu Ala Ala Ala Lys Gly Gly Gly Gly Ser Glu
1               5                   10                  15

Ala Ala Ala Lys Gly Gly Gly Gly Ser
            20                  25

<210> SEQ ID NO 66
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 66

Gly Gly Gly Gly Ser Gly Gly Gly Gly Ser Glu Ala Ala Ala Lys Gly
1               5                   10                  15

Gly Gly Gly Ser Glu Ala Ala Ala Lys
            20                  25

<210> SEQ ID NO 67
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 67

Glu Ala Ala Ala Lys Gly Gly Gly Gly Ser Glu Ala Ala Ala Lys Gly
1               5                   10                  15

Gly Gly Gly Ser Gly Gly Gly Gly Ser
            20                  25

<210> SEQ ID NO 68
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 68

Gly Gly Gly Gly Ser Glu Ala Ala Ala Lys Gly Gly Gly Gly Ser Glu
1               5                   10                  15

Ala Ala Ala Lys Glu Ala Ala Ala Lys
            20                  25

<210> SEQ ID NO 69
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 69

Glu Ala Ala Ala Lys Glu Ala Ala Ala Lys Gly Gly Gly Gly Ser Gly
1               5                   10                  15

Gly Gly Gly Ser Glu Ala Ala Ala Lys
            20                  25

<210> SEQ ID NO 70
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 70

```
Gly Gly Gly Gly Ser Gly Gly Gly Ser Glu Ala Ala Lys Glu
1               5                   10                  15

Ala Ala Ala Lys Gly Gly Gly Gly Ser
                20              25
```

<210> SEQ ID NO 71
<211> LENGTH: 79
<212> TYPE: PRT
<213> ORGANISM: Artificial Sequence
<220> FEATURE:
<223> OTHER INFORMATION: Protein translated from synthetic DNA

<400> SEQUENCE: 71

```
Ala Glu Ala Glu Ala Lys Ala Lys Ala Glu Ala Glu Ala Lys Ala His
1               5                   10                  15

Ala Glu Ala Glu Ala Lys Ala Lys Ala Asn Ala Glu Ala His Ala Lys
                20                  25                  30

Ala Glu Ala Glu Ala Lys Ser Lys Ala Glu Ala Glu Ala Lys Ala Lys
            35                  40                  45

Ala Glu Ala Glu Ala Lys Ala Lys Ala Glu Ala Glu Ala Lys Ala Lys
        50                  55                  60

Glu Ala Ala Ala Lys Glu Ala Ala Ala Lys Glu Ala Ala Ala Lys
65                  70                  75
```

<210> SEQ ID NO 72
<211> LENGTH: 63
<212> TYPE: PRT
<213> ORGANISM: Artificial Sequence
<220> FEATURE:
<223> OTHER INFORMATION: Protein translated from synthetic DNA

<400> SEQUENCE: 72

```
Ala Glu Ala Glu Ala Lys Ala Arg Ala Glu Ala Glu Ala Arg Ala Lys
1               5                   10                  15

Ala Glu Ala Glu Tyr Lys Ala Lys Ala Glu Ala Glu Ala His Ala Lys
                20                  25                  30

Ala Glu Ala Glu Ala His Ala Lys Ala Glu Ala Glu Ala Lys Ala Lys
            35                  40                  45

Glu Ala Ala Ala Lys Glu Ala Ala Ala Lys Glu Ala Ala Ala Lys
50                  55                  60
```

<210> SEQ ID NO 73
<211> LENGTH: 32
<212> TYPE: PRT
<213> ORGANISM: Artificial Sequence
<220> FEATURE:
<223> OTHER INFORMATION: Protein translated from synthetic DNA

<400> SEQUENCE: 73

```
Ala Glu Ala Glu Ala Arg Ala Lys Ala Glu Ala Glu Ala His Ala Lys
1               5                   10                  15

Ala Glu Cys Glu Ala Lys Ala Lys Ala Glu Tyr Glu Ala Lys Ala Lys
                20                  25                  30
```

<210> SEQ ID NO 74
<211> LENGTH: 36
<212> TYPE: PRT
<213> ORGANISM: Artificial Sequence
<220> FEATURE:
<223> OTHER INFORMATION: Protein translated from synthetic DNA

<400> SEQUENCE: 74

```
Ala Glu Ala Glu Ala Lys Ala Lys Ala Glu Ala Glu Ala Lys Ala Lys
1               5                   10                  15

Ala Glu Ala Glu Ala Lys Ala Lys Ala Asn Ala Tyr Ala Ser Ala Lys
                20                  25                  30

Ala Glu Ala Lys
        35
```

<210> SEQ ID NO 75
<211> LENGTH: 32
<212> TYPE: PRT
<213> ORGANISM: Artificial Sequence
<220> FEATURE:
<223> OTHER INFORMATION: Protein translated from synthetic DNA

<400> SEQUENCE: 75

```
Ala Glu Leu Glu Gly Lys Ala Lys Ala Glu Phe Glu Ala Lys Leu Lys
1               5                   10                  15

Ser Glu Leu Glu Ala Lys Ala Lys Ala Glu Ala Glu Ala Lys Ala Lys
                20                  25                  30
```

<210> SEQ ID NO 76
<211> LENGTH: 24
<212> TYPE: PRT
<213> ORGANISM: Artificial Sequence
<220> FEATURE:
<223> OTHER INFORMATION: Protein translated from synthetic DNA

<400> SEQUENCE: 76

```
Ala Glu Ala Glu Cys Lys Ala Lys Ala Glu Phe Glu Ala Lys Ala Lys
1               5                   10                  15

Ala Glu Ala Glu Ala Lys Ala Lys
                20
```

<210> SEQ ID NO 77
<211> LENGTH: 8
<212> TYPE: PRT
<213> ORGANISM: Artificial Sequence
<220> FEATURE:
<223> OTHER INFORMATION: Protein translated from synthetic DNA

<400> SEQUENCE: 77

```
Ala Glu Ala Asn Ala Lys Ala His
1               5
```

<210> SEQ ID NO 78
<211> LENGTH: 8
<212> TYPE: PRT
<213> ORGANISM: Artificial Sequence
<220> FEATURE:
<223> OTHER INFORMATION: Protein translated from synthetic DNA

<400> SEQUENCE: 78

```
Ala Glu Ala Glu Phe Lys Ala His
1               5
```

<210> SEQ ID NO 79
<211> LENGTH: 24
<212> TYPE: PRT
<213> ORGANISM: Artificial Sequence
<220> FEATURE:
<223> OTHER INFORMATION: Protein translated from synthetic DNA

<400> SEQUENCE: 79

```
Ala Glu Leu Glu Ala Lys Ala Lys Phe Glu Ala Glu Ala Lys Ala Lys
```

Ala Glu Ala Glu Ala Lys Ala Lys
            20

<210> SEQ ID NO 80
<211> LENGTH: 25
<212> TYPE: PRT
<213> ORGANISM: Artificial Sequence
<220> FEATURE:
<223> OTHER INFORMATION: Protein translated from synthetic DNA

<400> SEQUENCE: 80

Gly Gly Gly Gly Ser Glu Ala Ala Ala Lys Gly Gly Gly Gly Ser Gly
1               5                   10                  15

Gly Gly Gly Ser Glu Ala Ala Ala Lys
            20                  25

<210> SEQ ID NO 81
<211> LENGTH: 30
<212> TYPE: DNA
<213> ORGANISM: Artificial Sequence
<220> FEATURE:
<223> OTHER INFORMATION: Synthetic DNA

<400> SEQUENCE: 81
cgccatatga tggatgctga tttaggccac                                      30

<210> SEQ ID NO 82
<211> LENGTH: 29
<212> TYPE: DNA
<213> ORGANISM: Artificial Sequence
<220> FEATURE:
<223> OTHER INFORMATION: Synthetic DNA

<400> SEQUENCE: 82
ccgctcgagt taatttaatt tacccgcac                                       29

<210> SEQ ID NO 83
<211> LENGTH: 25
<212> TYPE: DNA
<213> ORGANISM: Artificial Sequence
<220> FEATURE:
<223> OTHER INFORMATION: Synthetic DNA

<400> SEQUENCE: 83
cgccatatga atgactcgat attct                                           25

<210> SEQ ID NO 84
<211> LENGTH: 28
<212> TYPE: DNA
<213> ORGANISM: Artificial Sequence
<220> FEATURE:
<223> OTHER INFORMATION: Synthetic DNA

<400> SEQUENCE: 84
ccgctcgagt gcggccgcaa gctttcag                                        28

<210> SEQ ID NO 85
<211> LENGTH: 33
<212> TYPE: DNA
<213> ORGANISM: Artificial Sequence
<220> FEATURE:
<223> OTHER INFORMATION: Synthetic DNA

<400> SEQUENCE: 85
ccgctcgagt tagtactgat tgaagatctg ctg  33

<210> SEQ ID NO 86
<211> LENGTH: 27
<212> TYPE: DNA
<213> ORGANISM: Artificial Sequence
<220> FEATURE:
<223> OTHER INFORMATION: Synthetic DNA

<400> SEQUENCE: 86
cgccatatgg agttttcaa aaagacg  27

<210> SEQ ID NO 87
<211> LENGTH: 72
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (25)..(25)
<223> OTHER INFORMATION: n is a, c, g, t or u
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: misc_feature
<222> LOCATION: (34)..(34)
<223> OTHER INFORMATION: n is a, c, g, t or u
<220> FEATURE:
<221> NAME/KEY: misc_feature
<222> LOCATION: (37)..(37)
<223> OTHER INFORMATION: n is a, c, g, t or u
<220> FEATURE:
<221> NAME/KEY: misc_feature
<222> LOCATION: (40)..(40)
<223> OTHER INFORMATION: n is a, c, g, t or u
<220> FEATURE:
<221> NAME/KEY: misc_feature
<222> LOCATION: (43)..(43)
<223> OTHER INFORMATION: n is a, c, g, t or u
<220> FEATURE:
<221> NAME/KEY: misc_feature
<222> LOCATION: (46)..(46)
<223> OTHER INFORMATION: n is a, c, g, t or u

<400> SEQUENCE: 87
tttagcctta gcttccgcct ccgcnyknvv nyknvvnthn vvnthnvvtt tagccttagc  60
ttccgcctcc gc  72

<210> SEQ ID NO 88
<211> LENGTH: 46
<212> TYPE: DNA
<213> ORGANISM: Artificial Sequence
<220> FEATURE:
<223> OTHER INFORMATION: Synthetic DNA

<400> SEQUENCE: 88
gccatggatg ctgatttagg ccaccagacg ttgggatcca atgatg  46

<210> SEQ ID NO 89
<211> LENGTH: 49
<212> TYPE: DNA
<213> ORGANISM: Artificial Sequence
<220> FEATURE:
<223> OTHER INFORMATION: Synthetic DNA

<400> SEQUENCE: 89
gctaaggcta aagaattcgc catggataat gactcgatat tcttttcac          49

<210> SEQ ID NO 90
<211> LENGTH: 33
<212> TYPE: DNA
<213> ORGANISM: Artificial Sequence
<220> FEATURE:
<223> OTHER INFORMATION: Synthetic DNA

<400> SEQUENCE: 90
catgccatgg agtttttcaa aaagacggca ctt                           33

<210> SEQ ID NO 91
<211> LENGTH: 20
<212> TYPE: DNA
<213> ORGANISM: Artificial Sequence
<220> FEATURE:
<223> OTHER INFORMATION: Synthetic DNA

<400> SEQUENCE: 91
gaattcgaag ctgcggcaaa                                          20

<210> SEQ ID NO 92
<211> LENGTH: 21
<212> TYPE: DNA
<213> ORGANISM: Artificial Sequence
<220> FEATURE:
<223> OTHER INFORMATION: Synthetic DNA

<400> SEQUENCE: 92
gaattcggtg gtggcggttc g                                        21

<210> SEQ ID NO 93
<211> LENGTH: 29
<212> TYPE: DNA
<213> ORGANISM: Artificial Sequence
<220> FEATURE:
<223> OTHER INFORMATION: Synthetic DNA

<400> SEQUENCE: 93
ctaaatcagc atccatggtt ttgccgcag                                29

<210> SEQ ID NO 94
<211> LENGTH: 32
<212> TYPE: DNA
<213> ORGANISM: Artificial Sequence
<220> FEATURE:
<223> OTHER INFORMATION: Synthetic DNA

<400> SEQUENCE: 94
gtcattatcc atgcccatg gttttgccgc ag                             32

<210> SEQ ID NO 95
<211> LENGTH: 32
<212> TYPE: DNA
<213> ORGANISM: Artificial Sequence
<220> FEATURE:
<223> OTHER INFORMATION: Synthetic DNA

<400> SEQUENCE: 95
tttgaaaaac tccatccatg gttttgccgc ag                            32

<210> SEQ ID NO 96

```
<211> LENGTH: 30
<212> TYPE: DNA
<213> ORGANISM: Artificial Sequence
<220> FEATURE:
<223> OTHER INFORMATION: Synthetic DNA

<400> SEQUENCE: 96
ctaaatcagc atccatggcg aaccgccacc                                        30

<210> SEQ ID NO 97
<211> LENGTH: 33
<212> TYPE: DNA
<213> ORGANISM: Artificial Sequence
<220> FEATURE:
<223> OTHER INFORMATION: Synthetic DNA

<400> SEQUENCE: 97
gtcattatcc atggcccatg gcgaaccgcc acc                                    33

<210> SEQ ID NO 98
<211> LENGTH: 33
<212> TYPE: DNA
<213> ORGANISM: Artificial Sequence
<220> FEATURE:
<223> OTHER INFORMATION: Synthetic DNA

<400> SEQUENCE: 98
tttgaaaaac tccatccatg gcgaaccgcc acc                                    33

<210> SEQ ID NO 99
<211> LENGTH: 388
<212> TYPE: PRT
<213> ORGANISM: Artificial Sequence
<220> FEATURE:
<223> OTHER INFORMATION: Protein translated from synthetic DNA

<400> SEQUENCE: 99
```

Ala Glu Ala Asn Ala Lys Ala His Gly Gly Gly Ser Gly Gly Gly
 1               5                  10                  15

Gly Ser Met Lys Tyr Leu Leu Pro Thr Ala Ala Ala Gly Leu Leu
                20                  25                  30

Leu Ala Ala Gln Pro Ala Met Ala Met Glu Phe Phe Lys Lys Thr Ala
            35                  40                  45

Leu Ala Ala Leu Val Met Gly Phe Ser Gly Ala Ala Leu Ala Leu Pro
    50                  55                  60

Asn Ile Thr Ile Leu Ala Thr Gly Gly Thr Ile Ala Gly Gly Gly Asp
65                  70                  75                  80

Ser Ala Thr Lys Ser Asn Tyr Thr Ala Gly Lys Val Gly Val Glu Asn
                85                  90                  95

Leu Val Asn Ala Val Pro Gln Leu Lys Asp Ile Ala Asn Val Lys Gly
            100                 105                 110

Glu Gln Val Val Asn Ile Gly Ser Gln Asp Met Asn Asp Asp Val Trp
        115                 120                 125

Leu Thr Leu Ala Lys Lys Ile Asn Thr Asp Cys Asp Lys Thr Asp Gly
    130                 135                 140

Phe Val Ile Thr His Gly Thr Asp Thr Met Glu Glu Thr Ala Tyr Phe
145                 150                 155                 160

Leu Asp Leu Thr Val Lys Cys Asp Lys Pro Val Val Met Val Gly Ala
                165                 170                 175

Met Arg Pro Ser Thr Ser Met Ser Ala Asp Gly Pro Phe Asn Leu Tyr
            180                 185                 190

-continued

Asn Ala Val Val Thr Ala Ala Asp Lys Ala Ser Ala Asn Arg Gly Val
            195                 200                 205

Leu Val Val Met Asn Asp Thr Val Leu Asp Gly Arg Asp Val Thr Lys
        210                 215                 220

Thr Asn Thr Thr Asp Val Ala Thr Phe Lys Ser Val Asn Tyr Gly Pro
225                 230                 235                 240

Leu Gly Tyr Ile His Asn Gly Lys Ile Asp Tyr Gln Arg Thr Pro Ala
            245                 250                 255

Arg Lys His Thr Ser Asp Thr Pro Phe Asp Val Ser Lys Leu Asn Glu
        260                 265                 270

Leu Pro Lys Val Gly Ile Val Tyr Asn Tyr Ala Asn Ala Ser Asp Leu
            275                 280                 285

Pro Ala Lys Ala Leu Val Asp Ala Gly Tyr Asp Gly Ile Val Ser Ala
        290                 295                 300

Gly Val Gly Asn Gly Asn Leu Tyr Lys Thr Val Phe Asp Thr Leu Ala
305                 310                 315                 320

Thr Ala Ala Lys Asn Gly Thr Ala Val Val Arg Ser Ser Arg Val Pro
            325                 330                 335

Thr Gly Ala Thr Thr Gln Asp Ala Glu Val Asp Asp Ala Lys Tyr Gly
        340                 345                 350

Phe Val Ala Ser Gly Thr Leu Asn Pro Gln Lys Ala Arg Val Leu Leu
            355                 360                 365

Gln Leu Val Leu Thr Gln Thr Lys Asp Pro Gln Gln Ile Gln Gln Ile
        370                 375                 380

Phe Asn Gln Tyr
385

<210> SEQ ID NO 100
<211> LENGTH: 388
<212> TYPE: PRT
<213> ORGANISM: Artificial Sequence
<220> FEATURE:
<223> OTHER INFORMATION: Protein translated from synthetic DNA

<400> SEQUENCE: 100

Ala Glu Ala Glu Phe Lys Ala His Gly Gly Gly Ser Glu Ala Ala
1               5                   10                  15

Ala Lys Met Lys Tyr Leu Leu Pro Thr Ala Ala Gly Leu Leu Leu
            20                  25                  30

Leu Ala Ala Gln Pro Ala Met Ala Met Glu Phe Phe Lys Lys Thr Ala
        35                  40                  45

Leu Ala Ala Leu Val Met Gly Phe Ser Gly Ala Ala Leu Ala Leu Pro
    50                  55                  60

Asn Ile Thr Ile Leu Ala Thr Gly Gly Thr Ile Ala Gly Gly Gly Asp
65                  70                  75                  80

Ser Ala Thr Lys Ser Asn Tyr Thr Ala Gly Lys Val Gly Val Glu Asn
            85                  90                  95

Leu Val Asn Ala Val Pro Gln Leu Lys Asp Ile Ala Asn Val Lys Gly
        100                 105                 110

Glu Gln Val Val Asn Ile Gly Ser Gln Asp Met Asn Asp Asp Val Trp
    115                 120                 125

Leu Thr Leu Ala Lys Lys Ile Asn Thr Asp Cys Asp Lys Thr Asp Gly
        130                 135                 140

Phe Val Ile Thr His Gly Thr Asp Thr Met Glu Glu Thr Ala Tyr Phe
145                 150                 155                 160

```
Leu Asp Leu Thr Val Lys Cys Asp Lys Pro Val Val Met Val Gly Ala
            165                 170                 175

Met Arg Pro Ser Thr Ser Met Ser Ala Asp Gly Pro Phe Asn Leu Tyr
            180                 185                 190

Asn Ala Val Val Thr Ala Ala Asp Lys Ala Ser Ala Asn Arg Gly Val
            195                 200                 205

Leu Val Val Met Asn Asp Thr Val Leu Asp Gly Arg Asp Val Thr Lys
            210                 215                 220

Thr Asn Thr Thr Asp Val Ala Thr Phe Lys Ser Val Asn Tyr Gly Pro
225                 230                 235                 240

Leu Gly Tyr Ile His Asn Gly Lys Ile Asp Tyr Gln Arg Thr Pro Ala
            245                 250                 255

Arg Lys His Thr Ser Asp Thr Pro Phe Asp Val Ser Lys Leu Asn Glu
            260                 265                 270

Leu Pro Lys Val Gly Ile Val Tyr Asn Tyr Ala Asn Ala Ser Asp Leu
            275                 280                 285

Pro Ala Lys Ala Leu Val Asp Ala Gly Tyr Asp Gly Ile Val Ser Ala
            290                 295                 300

Gly Val Gly Asn Gly Asn Leu Tyr Lys Thr Val Phe Asp Thr Leu Ala
305                 310                 315                 320

Thr Ala Ala Lys Asn Gly Thr Ala Val Val Arg Ser Ser Arg Val Pro
            325                 330                 335

Thr Gly Ala Thr Thr Gln Asp Ala Glu Val Asp Asp Ala Lys Tyr Gly
            340                 345                 350

Phe Val Ala Ser Gly Thr Leu Asn Pro Gln Lys Ala Arg Val Leu Leu
            355                 360                 365

Gln Leu Val Leu Thr Gln Thr Lys Asp Pro Gln Gln Ile Gln Gln Ile
            370                 375                 380

Phe Asn Gln Tyr
385

<210> SEQ ID NO 101
<211> LENGTH: 409
<212> TYPE: PRT
<213> ORGANISM: Artificial Sequence
<220> FEATURE:
<223> OTHER INFORMATION: Protein translated from synthetic DNA

<400> SEQUENCE: 101

Ala Glu Leu Glu Ala Lys Ala Lys Phe Glu Ala Glu Ala Lys Ala Lys
1               5                   10                  15

Ala Glu Ala Glu Ala Lys Ala Lys Glu Ala Ala Ala Lys Gly Gly Gly
            20                  25                  30

Gly Ser Glu Ala Ala Ala Lys Met Lys Tyr Leu Leu Pro Thr Ala Ala
            35                  40                  45

Ala Gly Leu Leu Leu Leu Ala Ala Gln Pro Ala Met Ala Met Glu Phe
            50                  55                  60

Phe Lys Lys Thr Ala Leu Ala Ala Leu Val Met Gly Phe Ser Gly Ala
65                  70                  75                  80

Ala Leu Ala Leu Pro Asn Ile Thr Ile Leu Ala Thr Gly Gly Thr Ile
            85                  90                  95

Ala Gly Gly Gly Asp Ser Ala Thr Lys Ser Asn Tyr Thr Ala Gly Lys
            100                 105                 110

Val Gly Val Glu Asn Leu Val Asn Ala Val Pro Gln Leu Lys Asp Ile
            115                 120                 125
```

-continued

```
Ala Asn Val Lys Gly Glu Gln Val Val Asn Ile Gly Ser Gln Asp Met
    130                 135                 140
Asn Asp Asp Val Trp Leu Thr Leu Ala Lys Lys Ile Asn Thr Asp Cys
145                 150                 155                 160
Asp Lys Thr Asp Gly Phe Val Ile Thr His Gly Thr Asp Thr Met Glu
                165                 170                 175
Glu Thr Ala Tyr Phe Leu Asp Leu Thr Val Lys Cys Asp Lys Pro Val
            180                 185                 190
Val Met Val Gly Ala Met Arg Pro Ser Thr Ser Met Ser Ala Asp Gly
        195                 200                 205
Pro Phe Asn Leu Tyr Asn Ala Val Val Thr Ala Ala Asp Lys Ala Ser
    210                 215                 220
Ala Asn Arg Gly Val Leu Val Val Met Asn Asp Thr Val Leu Asp Gly
225                 230                 235                 240
Arg Asp Val Thr Lys Thr Asn Thr Thr Asp Val Ala Thr Phe Lys Ser
                245                 250                 255
Val Asn Tyr Gly Pro Leu Gly Tyr Ile His Asn Gly Lys Ile Asp Tyr
            260                 265                 270
Gln Arg Thr Pro Ala Arg Lys His Thr Ser Asp Thr Pro Phe Asp Val
        275                 280                 285
Ser Lys Leu Asn Glu Leu Pro Lys Val Gly Ile Val Tyr Asn Tyr Ala
    290                 295                 300
Asn Ala Ser Asp Leu Pro Ala Lys Ala Leu Val Asp Ala Gly Tyr Asp
305                 310                 315                 320
Gly Ile Val Ser Ala Gly Val Gly Asn Gly Asn Leu Tyr Lys Thr Val
                325                 330                 335
Phe Asp Thr Leu Ala Thr Ala Ala Lys Asn Gly Thr Ala Val Val Arg
            340                 345                 350
Ser Ser Arg Val Pro Thr Gly Ala Thr Thr Gln Asp Ala Glu Val Asp
        355                 360                 365
Asp Ala Lys Tyr Gly Phe Val Ala Ser Gly Thr Leu Asn Pro Gln Lys
    370                 375                 380
Ala Arg Val Leu Leu Gln Leu Val Leu Thr Gln Thr Lys Asp Pro Gln
385                 390                 395                 400
Gln Ile Gln Gln Ile Phe Asn Gln Tyr
                405
```